United States Patent [19]
Fahrenkrug et al.

[11] Patent Number: 6,007,204
[45] Date of Patent: Dec. 28, 1999

[54] COMPACT OCULAR MEASURING SYSTEM

[75] Inventors: Corinn C. Fahrenkrug, Liverpool; Ervin Goldfain, Syracuse; Andrew J. Kugler, Jamesville; David G. Perkins, Syracuse; Howard A. Haines, III; William N. Cuipylo, both of Auburn, all of N.Y.

[73] Assignee: Welch Allyn, Inc., Skaneateles Falls, N.Y.

[21] Appl. No.: 09/089,807

[22] Filed: Jun. 3, 1998

[51] Int. Cl.⁶ ....................................................... A61B 3/10
[52] U.S. Cl. ............................................................. 351/221
[58] Field of Search .................................... 351/205, 211, 351/212, 219, 221, 246, 247; 356/121, 122, 123

[56] References Cited

U.S. PATENT DOCUMENTS

| | | |
|---|---|---|
| 4,141,652 | 2/1979 | Feinleib . |
| 4,162,828 | 7/1979 | Trachtman . |
| 4,399,356 | 8/1983 | Feinleib et al. . |
| 4,490,039 | 12/1984 | Bruckler et al. . |
| 4,518,854 | 5/1985 | Hutchin . |
| 4,666,298 | 5/1987 | Protz . |
| 4,724,522 | 2/1988 | Belgorod . |
| 4,725,138 | 2/1988 | Wirth et al. . |
| 4,838,679 | 6/1989 | Bille . |
| 4,933,872 | 6/1990 | Vandenberg et al. . |
| 5,113,064 | 5/1992 | Manhart . |
| 5,128,530 | 7/1992 | Ellerbroek et al. . |
| 5,229,889 | 7/1993 | Kittell . |
| 5,233,174 | 8/1993 | Zmek . |
| 5,287,165 | 2/1994 | Ulich et al. . |
| 5,300,766 | 4/1994 | Granger et al. . |
| 5,303,709 | 4/1994 | Dreher et al. . |
| 5,329,322 | 7/1994 | Yancey . |
| 5,455,645 | 10/1995 | Berger et al. . |
| 5,493,391 | 2/1996 | Schmutz . |
| 5,629,747 | 5/1997 | Miyake . |
| 5,629,765 | 5/1997 | Schmutz . |
| 5,632,282 | 5/1997 | Hay et al. . |
| 5,684,561 | 11/1997 | Yancey . |
| 5,777,719 | 7/1998 | Williams et al. ......................... 351/212 |

OTHER PUBLICATIONS

Modal wave–front estimation from phase derivative measurements Article, Optical Society of America, Ronald Cubalchini, Nov. 6, 1978 pp. 972–977.

Object.measure.of wave aberrations of the human eye.., vol. 11, No. 7/Jul. 1994/J. Opt. Soc.Am.A.1949 pp. 1949–1957.

Symposium of Wavefront Aberration of the Eye: W.N. Charman vol. 68, No. 8, pp. 574–583.

Nikon Hand–Held Ref Retinomax Sales Brochure, 6 pages, dated 1995.

*Primary Examiner*—George Manuel
*Attorney, Agent, or Firm*—Wall Marjama Bilinski & Burr

[57] ABSTRACT

Apparatus for determining refractive aberrations of the eye of a patient includes an instrument housing having a light source for projecting a substantially focused beam of light at the back of the eye of a patient, said substantially focused beam acting as a secondary source for a return light path of a fonned outgoing wavefront exiting said eye. An electronic sensor is disposed along said light return path, said electronic sensor having a light detecting surface disposed perpendicular to said return light path, and at least one microoptics array disposed between the electronic sensor and the eye along said return light path. The microoptics array includes plurality of lenslets disposed in a plane perpendicular to said light return path and positioned relative to said electronic sensor so as to substantially focus incremental portions of the outgoing wavefront onto the light detecting surface such that the deviations in the positions of the substantially focused portions impinging on said light detecting surface can be measured so as to determine aberrations of said wavefront. Preferably, at least one pair of conjugate lenses is disposed along said return light path and positioned between said eye and the microoptics array, the lenses of said conjugate pair having unequal focal lengths to allow the device to be used at an effective working distance from a patient

47 Claims, 7 Drawing Sheets

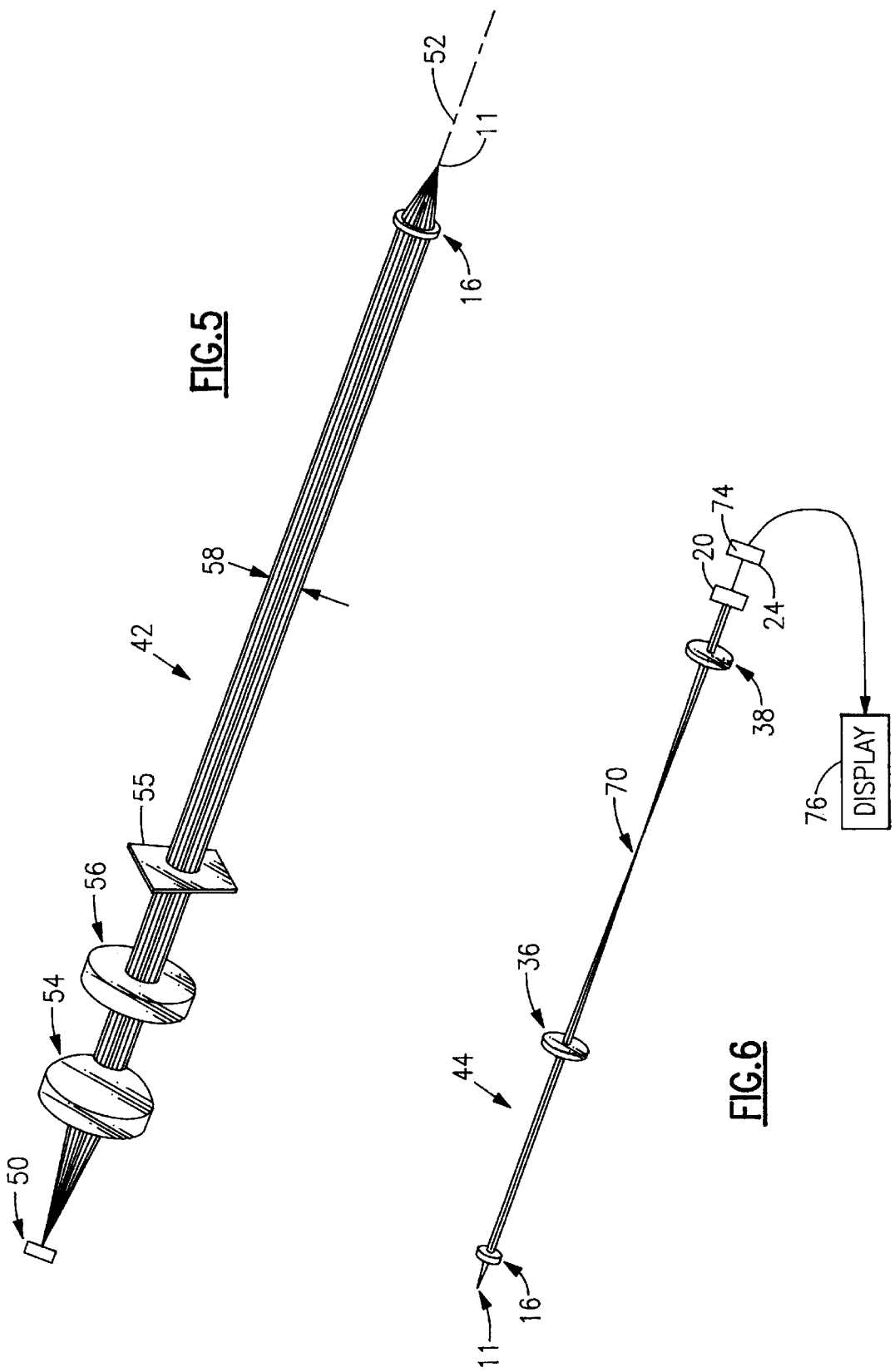

| $Dh_i$ | $DhL_i$ | $Dm_i$ | $DmL_i$ |
|---|---|---|---|
| 0.125 | 0.717 | −0.125 | −0.715 |
| 0.25 | 1.437 | −0.25 | −1.427 |
| 0.375 | 2.159 | −0.375 | −2.136 |
| 0.5 | 2.884 | −0.5 | −2.843 |
| 0.625 | 3.611 | −0.625 | −3.548 |
| 0.75 | 4.341 | −0.75 | −4.25 |
| 0.875 | 5.074 | −0.875 | −4.95 |
| 1 | 5.809 | −1 | −5.647 |
| 1.125 | 6.547 | −1.125 | −6.341 |
| 1.25 | 7.288 | −1.25 | −7.034 |
| 1.375 | 8.031 | −1.375 | −7.724 |
| 1.5 | 8.777 | −1.5 | −8.411 |
| 1.625 | 9.526 | −1.625 | −9.096 |
| 1.75 | 10.277 | −1.75 | −9.779 |
| 1.875 | 11.032 | −1.875 | −10.459 |
| 2 | 11.789 | −2 | −11.137 |
| 2.125 | 12.548 | −2.125 | −11.813 |
| 2.25 | 13.311 | −2.25 | −12.487 |
| 2.375 | 14.076 | −2.375 | −13.158 |
| 2.5 | 14.844 | −2.5 | −13.826 |
| 2.625 | 15.615 | −2.625 | −14.493 |
| 2.75 | 16.389 | −2.75 | −15.157 |
| 2.875 | 17.166 | −2.875 | −15.819 |
| 3 | 17.945 | −3 | −16.479 |
| 3.125 | 18.728 | −3.125 | −17.136 |
| 3.25 | 19.513 | −3.25 | −17.791 |
| 3.375 | 20.301 | −3.375 | −18.444 |
| 3.5 | 21.093 | −3.5 | −19.095 |
| 3.625 | 21.887 | −3.625 | −19.744 |
| 3.75 | 22.684 | −3.75 | −20.39 |
| 3.875 | 23.484 | −3.875 | −21.034 |
| 4 | 24.287 | −4 | −21.676 |

| $Dh_i$ | $DhL_i$ | $Dm_i$ | $DmL_i$ |
|---|---|---|---|
| 0.125 | 0.273 | −0.125 | −0.29 |
| 0.25 | 0.53 | −0.25 | −0.599 |
| 0.375 | 0.773 | −0.375 | −0.929 |
| 0.5 | 1.002 | −0.5 | −1.282 |
| 0.625 | 1.219 | −0.625 | −1.661 |
| 0.75 | 1.425 | −0.75 | −2.068 |
| 0.875 | 1.621 | −0.875 | −2.507 |
| 1 | 1.807 | −1 | −2.981 |
| 1.125 | 1.984 | −1.125 | −3.496 |
| 1.25 | 2.153 | −1.25 | −4.056 |
| 1.375 | 2.314 | −1.375 | −4.668 |
| 1.5 | 2.467 | −1.5 | −5.339 |
| 1.625 | 2.614 | −1.625 | −6.079 |
| 1.75 | 2.755 | −1.75 | −6.898 |
| 1.875 | 2.89 | −1.875 | −7.81 |
| 2 | 3.019 | −2 | −8.832 |
| 2.125 | 3.143 | −2.125 | −9.985 |
| 2.25 | 3.262 | −2.25 | −11.296 |
| 2.375 | 3.377 | −2.375 | −12.798 |
| 2.5 | 3.487 | −2.5 | −14.54 |
| 2.625 | 3.593 | −2.625 | −16.58 |
| 2.75 | 3.695 | −2.75 | −19.006 |
| 2.875 | 3.794 | −2.875 | −21.935 |
| 3 | 3.889 | −3 | −25.544 |
| 3.125 | 3.981 | −3.125 | −30.1 |
| 3.25 | 4.069 | −3.25 | −36.033 |
| 3.375 | 4.155 | −3.375 | −44.078 |
| 3.5 | 4.238 | −3.5 | −55.605 |
| 3.625 | 4.318 | −3.625 | −73.501 |
| 3.75 | 4.395 | −3.75 | −105.059 |
| 3.875 | 4.47 | −3.875 | −175.584 |
| 4 | 4.543 | −4 | −473.7 | ature
COMPACT OCULAR MEASURING SYSTEM

FIELD OF THE INVENTION

The invention relates to medical devices, and in particular to an compact, preferably hand-held apparatus for measuring the refractive eye aberrations. The apparatus can be adjusted to allow reliable refractive error to be measured for a variety of patient populations (children, adults).

BACKGROUND OF THE INVENTION

It is known that the eye receives light which is ideally focused onto the retina through the cumulative convergence provided by the cornea, the lens, and fluids on the eyeball. Refractive errors affect the focus point of the light such that for nearsighted (myopic) people, the focus falls short of the retina allowing images close to the eye to be clearly viewed while blurring images at a distance. Conversely, farsightedness (hyperopic) also fails to provide a focus. Refractometry allows correction via lenses to affect changes due to hyperopia, myopia, and astigmatism, among others.

In certain populations, detection of refractive errors can be performed to prevent irreversible loss of vision. In preschool children, a malady known as amblyopia, otherwise known as "lazy eye", is particularly important. Approximately 5 percent of all children are either born with or develop a form of this malady. As an untreated child having this malady becomes older, neural development in the brain tends to permanently suppress vision in the diseased eye. This prevents proper binocular vision in the child, with this impairment becoming irreversible after about seven years of age. Current medical academy guidelines suggest diagnosis and detection should be made as early as possible, and suggest physicians target the age of three as the proper screening age. A critical aspect to this screening is measurement of the refractive state of the patient's eyes for comparison to known standards.

Photorefractors are known devices which use the red reflex produced by the eye as a method for determining refractive error. These devices produce a flash, either on or off axis with a peephole, and record the resulting reflex which is reflected from the retina. For example, U.S. Pat. No. 4,989,968, issued to Freedman, discloses a small slit aperture and a light source positioned 0.5 mm from the slit aperture. In use, a photograph is taken of the red reflex of a single subject which appears at the aperture when the light source is flashed. A second photograph is taken with the slit aperture and light source rotated 90 degrees from a position used to take the first photograph. Examination of the shape and intensity of the red reflexes which appear in these photographs allows a trained user to detect whether a large refractive error is present.

The primary problem with this device in serving the screening needs of small children is that the interpretation of the result (a photograph) is both time consuming and subjective, making diagnosis impractical on a real time basis. The interpretation consists of identifying the presence of a "defect", but does not provide quantitative information concerning the refractive error, therefore making it difficult to diagnose children or others whose condition is marginal. The device suffers from a "dead zone" which is a refractive range, close to zero diopters, in which no reading is produced. This prevents measurement of a percentage of the target population. In addition, the device also falls short of being compact and held in a single hand during use, as is desirable in the field for screening applications. Another problem with the instant device is that it does not perform effectively on patients having smaller pupils. This prevents a segment of children from being measured in a normal screening environment.

Variations of these devices include CCD camera-based systems. For example, in U.S. Pat. No. 5,632,282, issued to Hay, there is a described method of automatically analyzing the intensity levels of the retinal reflection from a subject's eyes to determine whether pathologic conditions are present. If implemented by a data processor, this method addresses the real time problems confronted by the device of Freedman. However, the problems of "dead zone", lack of quantitative results, compactness of the size of the instrument employing this method, and the requirement for large pupil size are not addressed.

There are known autorefractors which can determine, quantitatively, to a limited extent, refractive differences between the ideal and an aberrative eye.

In known devices, such as manufactured by Nikon, the device requires a number of moving optical elements in order to null the patient's refractive error to obtain a reading. This nulling increases the refractive range which can be measured at the expense of test time and accuracy within the range. These commercial autorefractors require very short working distances to achieve measurement.

Therefore, a problem which exists concerns the adaptability of such apparatus. Typically, young children are distressed when presented with diagnostic instruments close to their face. This makes devices, such as the "Retinomax" manufactured by Nikon, for example, unusable on many children. In children which will tolerate such a device, the close proximity of the instrument causes accommodation, which tends to make the readings less accurate. The refractive state of an eye depends on what the patient is focusing on. For example, when a patient focuses on a near object, his or her refractive state would appear to be near sighted (myopic), even though the patient may not be. The refractive state which is of interest for screening, as well as for prescribing corrective lenses is the refractive state when the patients eye is relaxed and he or she is focused at a distance. Ideally, this distance is infinity, but in practice, it varies from 20 feet to 6 feet for acuity tests, and approximately 65 cm in retinoscopy evaluations.

Adult patients can be instructed to look at a distant object, such as a chart on a wall, even though objects or people may be closer to them. However, the natural instinct of children is to focus on the closest object which in the screening environment is typically the practitioner or the device. Consequently, the closer the device is to a child patient, the more he or she will accommodate, and the more erroneously myopic the refractive measurement will be compared to the true value. The moving optical elements make the time required for examination longer, which is also less suitable for the low attention span of young children. It is also desirable to achieve higher refractive assessment accuracy in the specific ranges for target populations. For example, American children typically have refractive errors in the range of −1 Diopters to +4 Diopters at age three. Adults are more typically myopic and average approximately −3 Diopters (+1 Diopters to −5 Diopters typically).

SUMMARY OF THE INVENTION

A primary object of the present invention is to improve the state of the art of refractive error measuring devices.

Another primary object of the present invention is to provide an autorefractor apparatus which can operate at longer working distances than known devices of this type, and which is compact and preferably hand held.

It is another primary object of the present invention to provide an autorefractor which produces quantitative refractive state information in real time, and without a deadzone within the range of measurement.

It is another primary object of the present invention to provide an autorefractor utilizing a measurement system which can be adjusted to allow optimum effectivity over literally any targeted patient population by achieving higher accuracy within a specific range of refractive error.

Therefore, and according to a preferred aspect of the present invention, there is provided an apparatus for determining refractive errors of the eye, said apparatus comprising:

a hand-held housing;

illumination means including at least one source of illumination disposed in said housing for projecting a beam of light into the eye of a patient along an illumination axis, said beam forming a secondary source on the back of the eye for a return light path of an outgoing generated wavefront from said eye;

measurement means disposed in said housing including light sensing means disposed along said light return path, said light sensing means including a light detection surface; and at least one microoptics array disposed between said electronic sensor and said eye along said return light path, said microoptics array comprising a plurality of lenslets planarly disposed, said plurality of lenslets and said light detection surface being arranged parallel to each other and perpendicularly to said light return path, said microoptics array being positioned relative to said light sensing means so as to substantially focus portions of said formed wavefront onto said light detection surface, said measurement means further including means for detecting deviations in the positions of the substantially focused portions impinging on said light detecting surface so as to determine aberrations of said outgoing wavefront.

Preferably, the device includes at least one pair of conjugate lenses disposed along the return light path, preferably in which each of the lenses includes a different focal length. This allows the apparatus to be formed compactly and to operate at a suitable working distance, in the range of 1–80 cm, but typically in the range of 30–50 cm, between the apparatus and the eye of interest.

According to another preferred aspect of the present invention, there is provided a compact apparatus for determining refractive aberrations of the eye, said apparatus comprising:

a hand-held housing;

illumination means disposed in said housing for projecting a beam of light into the eye of a patient along an illumination axis, said beam forming a secondary source on the back of the eye for a return light path of an outgoing generated wavefront from said eye;

measurement means disposed in said housing including an electronic sensor disposed along said light return path, said electronic sensor having an imaging substrate;

at least one microoptics array disposed between said electronic sensor and said eye along said return light path, said microoptics array comprising a plurality of lenslets planarly disposed, said plurality of lenslets and said imaging substrate being arranged parallel to each other and perpendicularly to said light return path, said microoptics array being positioned relative to said electronic sensor so as to substantially focus portions of said formed wavefront onto said imaging substrate, said measurement means further including means for detecting deviations in the substantially focused portions impinging on said imaging substrate so as to determine aberrations of said outgoing wavefront, and at least one pair of conjugate lenses disposed along said light return path between the eye of interest and said microoptics array, each of said conjugate lenses having different focal lengths for allowing said housing to be used at a suitable working distance from a patient.

Preferably, the working distance can be any distance greater than 1 cm but is preferably in the range of 5–80 cm.

According to yet another preferred aspect of the present invention, there is provided a method of measuring refractive eye error, said method comprising:

projecting a light into an eye of interest, said light producing a point source and generating a representative wavefront from the eye along a return light path;

directing said wavefront through a pair of conjugate lenses onto a microoptics array having a series of planarly disposed lenslet elements, said conjugate lenses and said microoptics array being disposed along said return light path;

substantially focusing portions of said generated wavefront passing through said lenslet elements onto an imaging substrate; and measuring the deviations in the substantially focused portions of said generated wavefront on said imaging substrate so as to measure refractive error in the eye of interest.

Preferably, each of the conjugate lenses have different effective focal lengths, in which the method includes the step of separating said pair of conjugate lenses along said return light path by substantially the sum of the respective focal lengths of said lenses in order to enlarge or minify the beam diameter containing the wavefront at the microoptics array.

In a preferred arrangement, the distance between the conjugate lens closest to the microoptics array and the array can be optimized for minimizing corneal glare at the array.

In a preferred embodiment, a minified wavefront utilizing a microoptics array of an adequate pitch provides an increased optical power at each corresponding microoptics surface and allows the measurable diopters of the eye of interest to be manipulated at the array so as to improve the sensitivity of the device over specified diopter ranges, enabling the device to be especially useful for specific populations, such as young children having a diopter range which is distinct as compared to adult populations.

An advantage realized by the present invention is rapid quantitative refractive readings can be taken because there are no moving parts during the examination, thereby minimizing the required test time.

A further advantage realized by using a microoptics array and substantially focusing portions of the wavefront is that readings can be made over a range of refractive errors without a deadzone.

A further advantage realized by using a conjugate pair whose focal lengths are not equal is that the diopters presented at the lenslets can be manipulated with respect to those at the eye within a prescribed dynamic range to optimize refractive screening for target patient populations. More particularly, adjustment of the conjugate focal lengths so that the pupil image is minified at the lenslet with respect to the pupil provides enhanced sensitivity and accuracy of the device to cover different populations of eyes, for example, between a general eye care device suitable for adults and apparatus useful for small children, each said device having a high degree of accuracy and repeatability within their likely measurement range.

A further advantage realized by a preferred embodiment of the device is a greater working distance which can preclude the need to fog the patient or to accept the lower accuracy of close distance devices. This increased working distance also allows the device to be useful with young children who are distressed when instruments are held close to their faces.

Yet another advantage of the present invention is that the device is relatively compact and moreover can be contained in a lightweight hand held unit. Preferably, the unit is sufficiently compact to allow use with a single hand, leaving the other hand of the user free.

Another advantage of the preferred embodiment is the use of NIR laser light which simultaneously minimizes pupillary constriction, and can be projected as a small beam for easy entry into small pupils.

Yet another advantage is that the projected beam of illuminated light can be adjusted so as to vary the focus position on the back of the eye. This variation allows better accuracy for myopic or hyperopic conditions.

Still another advantage of the present invention is that the illumination and viewing systems can be placed in the device in a manner which reduces the number of required parts, further simplifying the assembly and manufacturability of the apparatus.

Another advantage of the present invention using the microoptics array and substantially focusing incremental portions of the waveform resulting from the retinal reflection is that higher order (other than merely sphere and cylindrical) aberrations can be computed. The measure of these aberrations have potential applications in screening target populations, such as contact lens wearers or PRK patients, who may be at increased risk for higher order defects.

Still another advantage of the present invention is that by including a position measurement system, inaccuracies due to differences in patient position with respect to the instrument can be minimized.

Yet another advantage is that fixating means are disposed for minimizing the problems of accommodation, thereby improving the overall accuracy and measurement time of the instrument.

These and other objects, features, and advantages will become apparent from the following Detailed Description of the Invention which should be read in conjunction with the accompanying drawings.

BRIEF DESCRIPTION OF THE DRAWINGS

FIG. 5 is a ray trace diagram of the illumination portion of the system illustrated in FIG. 4;

FIG. 6 is a ray trace diagram of the measurement portion of the system illustrated in FIG. 4;

DETAILED DESCRIPTION OF THE INVENTION

The following discussion relates to several different embodiments of an apparatus used for measuring eye refractive error. Throughout the course of the discussion which follows, several terms such as "front", "back", "top", "bottom", and the like are frequently used. These terms are used to provide a frame of reference in describing the accompanying drawings. Such terminology, however, should not be viewed as limiting of the inventive concepts of the present invention.

Figure 1:
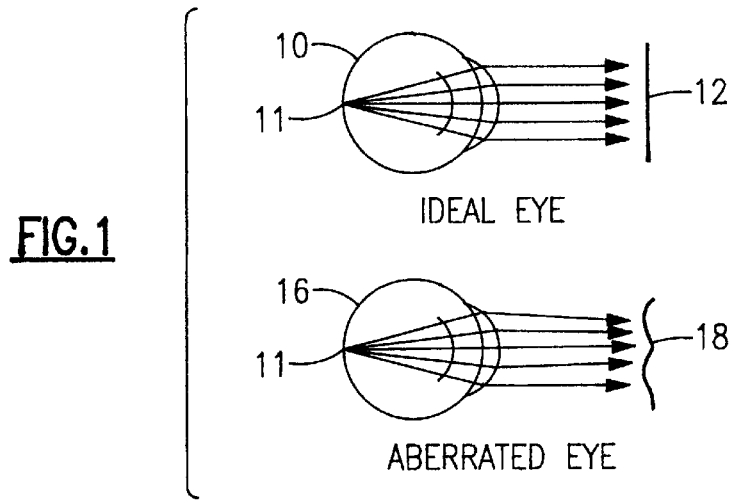
FIG. 1 is a schematic view illustrating differences between generated wavefronts exiting from an ideal eye and an aberrated eye, respectively.

For purposes of background, reference is first made to FIG. 1. When a beam of light is projected into an eye of interest, the light is focused onto the back of the eye by optics thereof and diffusely reflected by the retina. The outgoing beam is more or less focused and forms a secondary source 11 for light which exits the eye and generates a wavefront, as shown in FIG. 1. Herein, a secondary source is referred to as the image of the illuminating source or the fiducial mark (if used) onto the back of the eye created by the illuminating optics. The wavefront 12 of an ideal eye 10; that is, an eye substantially free from refractive errors, is defined by a set of substantially outgoing collimated rays and thereby forms a planar wavefront. On the other hand, the wavefront 18 generated by an aberrated eye 16 is defined by a series of non-collimated outgoing rays, generating a wavefront which deviates from the ideal planar form.

Figure 2:
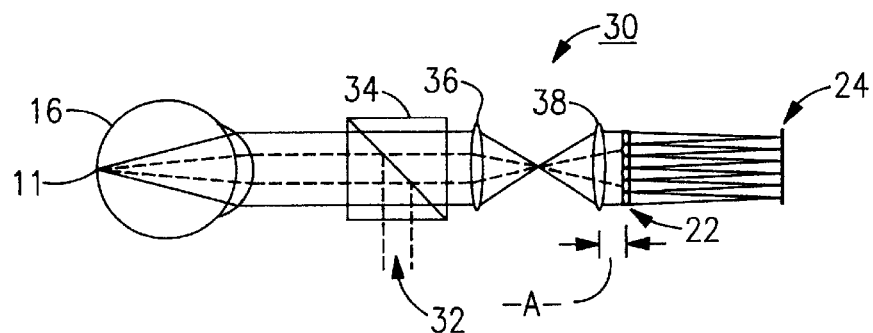
FIG. 2 is a diagrammatic view of a refractive error measuring system in accordance with a first embodiment of the present invention.

Referring to FIG. 2, a diagrammatic view is presented of a refractive error measuring system 30 in accordance with the present invention. A more detailed description follows, but in brief, a substantially collimated beam of light 32 is passed through a beam splitter 34 along an illumination axis which is then directed to the eye of interest. The collimated light 32 is focused as a secondary source 11 on the back of the eye 16, thereby producing the generated wavefront 18, FIG. 1, exiting from the eye along a return light path. The beam 32 according to a preferred arrangement can be adjusted, e.g. converged/diverged to adjust the point of focus, such as for young children.

A pair of conjugate lenses, 36, 38 described in greater detail below, direct the light to a microoptics array 20 where each of the incremental portions of the generated wavefront 18 are substantially focused onto an imaging substrate 24.

Figure 3:
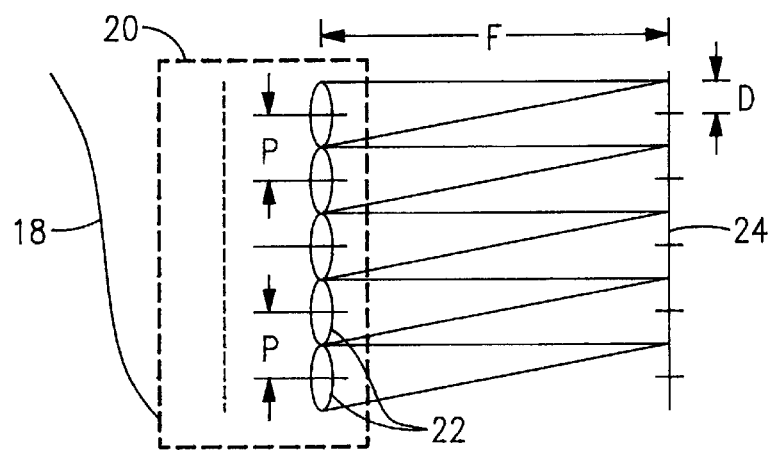
FIG. 3 is a partial schematic view of the microoptics array of the system of FIG. 2.

A novel component of the system described by the present invention, shown more particularly in FIG. 3, is the microoptics array 20 containing a plurality of small planarly disposed lenslet elements 22. Each of the lenslets 22 are evenly separated from one another by a dimension -P-, hereinafter referred to as pitch. Light from the generated wavefront 18, FIG. 1, entering the microoptics array 20 is focused by the lenslets 22 onto an imaging substrate 24 or other detecting surface which is preferably placed at a suitable distance -F- from the lenslet elements. Incremental portions of the wavefront 18, FIG. 1, passing through a sufficient number of lenslets 22 are then focused onto the substrate 24 and the deviations -D- of the positions of the incremental portions relative to a known zero or "true" position can be used to compute refractive error relative to a known zero or ideal diopter value. This can be defined as an array of "zero" spots corresponding to a planar wavefront, such as that shown in FIG. 1. Details relating to the mathematical technique for estimating the wavefront are described in greater detail below.

Figure 4:
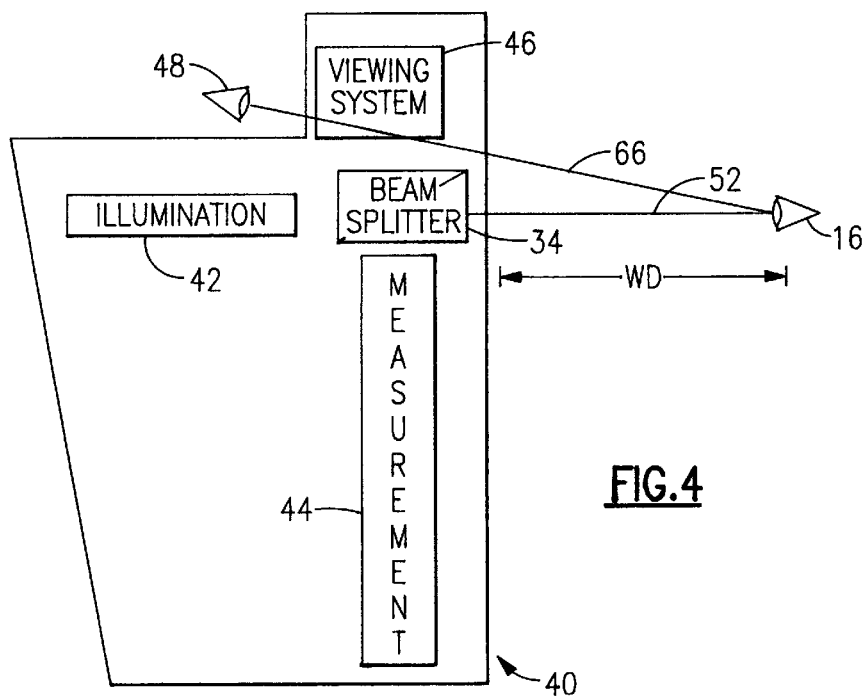
FIG. 4 is a block diagram representative of the refractive error measuring system of FIG. 2.

A block diagram of the apparatus according to the present invention is herein described with reference to FIG. 4 including an instrument housing 40 having an interior sized for containing the described system 30, FIG. 2, having in particular three (3) major subassemblies; namely an illumination subassembly 42, a measurement subassembly 44, and a viewing subassembly 46 shown relative to a viewing eye 48. A preferred embodiment of each subassembly is shown in the following FIGS. 5–7 for use in the instrument housings, shown more particularly in FIGS. 8 and 9. An important feature of the present invention is that the instrument housing 40 can be situated for operation at a suitable working distance -WD- from the eye 16 of the patient. According to the present embodiment, a working distance of approximately 40 cm is suitable.

Each of the subassemblies 42, 44, 46 will be described prior to describing structural embodiments which employ the described subassemblies. Referring first to FIG. 5, a schematic diagram is shown for the illumination assembly 42, the purpose of which is to focus a beam of light onto the back of the eye 16; that is, onto the retina of a patient. According to this embodiment, a laser diode 50 is preferably used as an illumination source which projects monochromatic light in conjunction with a plano-convex singlet 54 disposed adjacent to a plano-concave singlet 56, the elements being arranged and aligned to produce a beam of substantially collimated light 58 which can be projected along the illumination axis 52 into the eye of interest, the light being focused onto the back thereof, as previously shown in FIG. 1.

More specifically, and according to this embodiment, the plano-convex singlet 54 and the plano-concave singlet 56 have effective focal lengths of approximately 25 mm and –50 mm, respectively, closed with an aperture 55 to produce a substantially collimated beam of light having a diameter of approximately 2.5 mm. The laser diode 50 emits near-infrared light having a wavelength of approximately 780 nm, so as not to constrict the pupil. Alternately, a halogen (or other broad-band) illumination source (not shown) could be substituted with adequate filtering. Still other lens systems could be utilized in lieu of the one herein described; for example, a single lens having a 60 mm effective focal length could be substituted for the lens pair of the present embodiment.

By modifying the distances between the plano-convex singlet 54 and the plano concave singlet 56, the beam of light projected can be made to be slightly divergent, or slightly convergent. This variation will create a best focus on the back of an eye which is slightly myopic or hyperopic, respectively. Illumination adjustment allows the system to be optimized for a likely refractive range of a targeted population.

Figure 7:
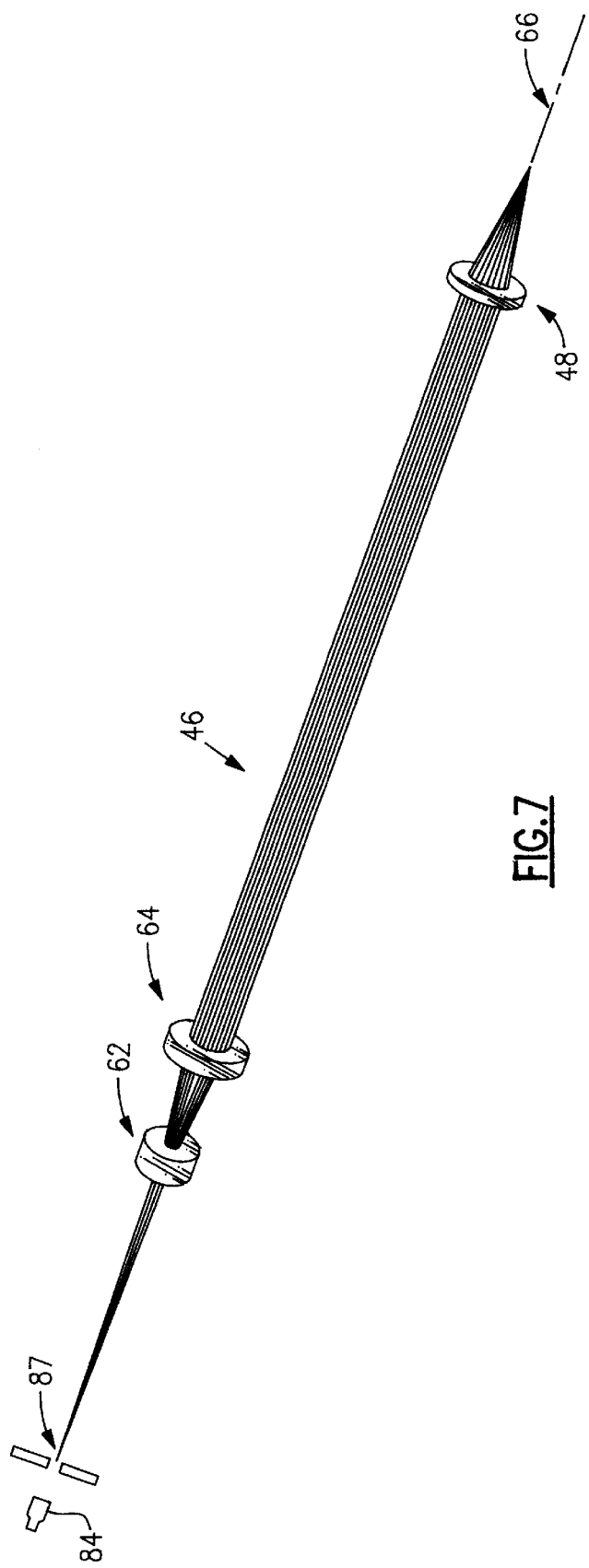
FIG. 7 is a ray trace diagram of the unfolded viewing portion of the system illustrated in FIG. 4.

As shown in FIG. 7, a schematic diagram of the major optical components of the viewing subassembly 46 is shown which is used to align the user's eye 48 to the illumination axis 52, FIG. 5, of the illuminating assembly 42, FIG. 5. The optics of the viewing subassembly 46 of the present embodiment include a plano-concave singlet 62 which is disposed adjacent to a plano-convex singlet 64.

According to the present embodiment shown, the first singlet 62 has an effective focal length of –8 mm, while the second singlet 64 has an effective focal length of approximately 22 mm. It should be apparent, however, that these parameters can also easily be varied.

Figure 8:
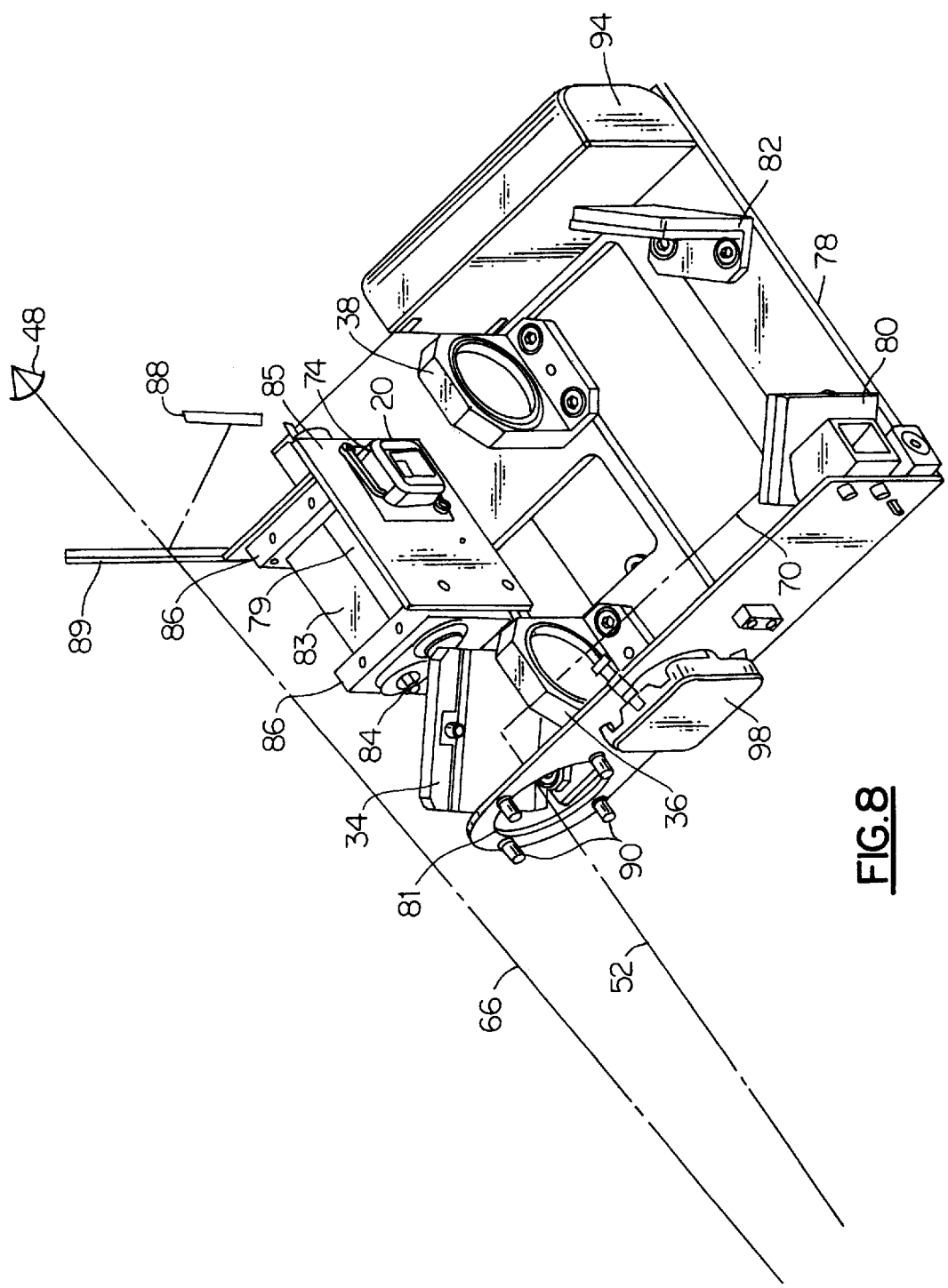
FIG. 8 is a partial interior view of the refractive error measuring system according to a first preferred embodiment according to the present invention.

As shown more clearly in the structural version of the apparatus shown in FIG. 8, the viewing subassembly 46, shown in phantom, is maintained either at a side or at a height above the projected beam 58, of FIG. 5 (approximately 8 degrees according to this embodiment).

As described more completely below, an alignment guide or pattern, such as a crosshairs (not shown), is targeted using a viewing window 89 which is aligned with a viewing port (not shown) and along a viewing axis 66 which is inclined relative to the illumination axis 52.

Alternately, the viewing subassembly 46 can include an eyepiece (not shown) and magnifying optics (not shown).

Referring now to FIG. 6, the measurement subassembly 44 includes a number of components used to direct the generated wavefront 18, FIG. 1, along a return light path 70 from the eye 16. A pair of fixed conjugate lenses 36, 38 are each placed between the eye of interest and the microoptics array 20 along the return light path 70. For purposes which are described in greater detail below, the conjugate pair are preferably separated from one another by substantially the sum of their respective and preferably unequal focal lengths.

According to the present embodiment, the first conjugate lens 36 is a plano-convex element having a focal length of approximately 150 mm and the second conjugate lens 38, also a plano-convex element has a focal length of about 63 mm, providing a total distance therebetween of approximately 213 mm.

The microoptics array 20 is further disposed along the return light path 70 from the second conjugate lens 38 and at a distance of approximately 17 mm from the second conjugate lens 38. An electronic sensor 74, such as a charge coupled device (CCD) or other imaging sensor having an imaging substrate 24 is then disposed at a predetermined distance therefrom. According to the present embodiment, the electronic sensor 74 is a Sony ICXO84AL, though other electronic imaging sensors, such as a Panasonic GP-MS-112 black and white video camera having either CCD or CMOS architecture, for example or others, can be substituted, each having appropriate processing circuitry as is known in the field, requiring no further discussion.

Referring to FIGS. 3 and 6, the microoptics array 20 according to the present embodiment, such as those manufactured and sold by Adaptive Optics Inc, of Boston, Mass., comprises a matrix of lenslet elements 22 disposed in a planar relationship which when positioned in the return light path 70 is orthogonal thereto. According to the present embodiment, the lenslets 22 each have an effective focal length of approximately 8 mm and are each separated from one another by approximately 0.50 mm. It will be readily apparent that each of these parameters can be suitably varied, for example, pitch in the range of approximately 0.25 mm to approximately 2 mm are adequate.

As previously noted, the incremental portions of the generated wavefront 18, FIG. 1, are substantially focused onto a imaging substrate 24 of the electronic sensor 74, which is disposed orthogonally to the light return path 70 and placed the predetermined distance -F- from the lenslets 22 of the microoptics array 20. Preferably, and according to this embodiment, the distance -F- between the microoptics array 20 and the imaging substrate 24 of the electronic sensor 74 is approximately 8 mm, which is the focal length of the lenslets 22.

In brief, light impinging on the imaging substrate 24 is detected by the electronic sensor 74 in a manner conventionally known. The image which is formed at the electronics sensor 74 consists of a matrix of spots, one for each lenslet 22. These spots are captured by the imaging substrate 24 at the distance -F- from the microoptics array 20. The distance -D-, FIG. 3, between the centroids of each of the spots is calculated and is used to determine the refractive power of the wavefront 18, FIG. 3, which created them. This power is corrected by the conjugate lens mapping function to interpolate the power at the eye. The optical power detected at the lenslet does not equal the optical power of the measured eye. Therefore, one needs to convert the diopter readings from the microoptics array to the patient's eye. This refractive error is reported to the user of the instrument through an attached LCD 76, shown schematically in FIG. 6. The principles for estimation of the formed wavefront, using Zernike polynomials are described in Journal of Optical Society of America, vol 69, No. 7 in an article by Cubalchini, the entire contents of which are herein incorporated by reference.

Referring now to FIG. 8, a particular embodiment of the above apparatus is herein described employing the above subassemblies 42, FIG. 5, 44, FIG. 6. 46, FIG. 7. The apparatus is shown in part as mounted to a support plate 78 contained within the housing 40, FIG. 4, shown only partially for the sake of clarity in describing the present embodiment. The basic components previously described in FIGS. 5–7 are utilized herein, but the return light path 70 is folded to maximize packaging into a conveniently sized housing.

The support plate 78 maintains each of the components herein described in a fixed relative position. The laser diode 50, FIG. 5, is supported within an illumination housing 79 along with suitable illuminating optics, such as described above with respect to FIG. 5, the illumination output being transmitted through a beam splitter 34 so as to project a beam of substantially collimated light along an illumination axis 52.

An adjacent housing 83 includes an LED 84 and aperture 87 for backlighting a cross-hair or other conveniently shaped alignment pattern (not shown), the pattern being placed in the viewing system and projected using a folding mirror 88 and a viewing window 89 disposed along the viewing axis 66 and aligned with the user's eye 48.

The viewing subassembly 46 is intended to provide to the practitioner a means to align the device to the patient's pupil. The alignment pattern (not shown) is projected onto the window 89 through a side train of lenses (not shown) and the folding mirror 88 such that the pattern appears to be at the same working distance as the patient's eye. According to this embodiment, the working distance -WD- is approximately 40 cm.

The entire viewing subassembly 46 is positioned off axis with respect to the illumination axis 52. The oblique position of the viewing subassembly 46 relative to the illumination subassembly 42 separates the viewing and illumination measurement paths, as opposed to a coaxial design which would require two or more beam splitters. Because of the relatively long working distance, the oblique position does not substantially affect the ability to align the patient's pupil to the optical axis of the instrument.

According to this embodiment, the main beam splitter 34 is disposed relative to the laser diode 50, FIG. 5, so as to be positioned 45 degrees relative to the illumination/measurement axis to direct light received from the eye of interest orthogonally along the return light path 70 to the first conjugate lens 36 mounted in a conventional manner to the support plate 78 and aligned with a pair of folding mirrors 80, 82 also aligned to fold the return light path, allowing convenient and compact packaging. The second conjugate lens 38 is disposed between the second folding mirror 82 and the microoptics array 20 which is attached along with the electronic sensor 74 to a vertical plate 85 attached to the support 86 for the illumination assembly and the LED generator housing 83 for the viewing assembly 46.

The return light path 70 therefore exits the eye 16, FIG. 2, and reenters the device through an existing port 81. The light is deflected by the beamsplitter 34 and then is directed through the first conjugate lens 36 and is folded by the mirrors 80, 82 through the interior of the housing 40 and finally to the second conjugate lens 38. The conjugates 36, 38 according to this embodiment are separated by the sum of the respective focal lengths of each lens.

As noted above and according to this specifically described embodiment, the first conjugate lens 36 has an effective focal length of approximately 150 mm and the second conjugate lens 38 has an effective focal length of approximately 63 mm. Therefore, the total folded distance between the first and second conjugate lenses 36, 38 is approximately 213 mm.

To insure that the proper working distance (40 cm according to this embodiment) is established between the first conjugate lens 36 and the patient eye 16, an ultrasonic distance measuring device 98 is included which provides an audible signal when the instrument is located at the proper distance. Alternately, distance measurement or range finding means such as, but not limited to, time of flight, phase detection, (e.g. ultrasonic, RF, IR) triangulation, or converging projections can be used to guide the user to position the device at the proper working distance. These distances can also be captured by the electronic sensor or microprocessor (not shown) to incorporate during the calculation of refractive error to improve the accuracy of the measurement.

In addition, the apparatus also preferably includes means for fixating the patient's gaze to ensure the patient's attention is directed to the port 81. According to a preferred embodiment, a series of flashing LED's 90 are provided adjacent the port 81. In another alternate embodiment, a signal generator (not shown) can emit an audible cue to direct the patient's gaze toward the port 81.

In use, the eye 16 is viewed through the window 89 using the alignment pattern (not shown) for aiming the apparatus, ensuring proper alignment of the illumination assembly 42. The light is then projected by the laser diode 50, FIG. 5, through the illumination lens system as a substantially collimated beam into the eye 16, FIG. 1. The return beam is then generated as a representative wavefront 18 which is guided through the pair of conjugate lenses 36, 38, as well as the beamsplitter 34, each of which is aligned with the microoptics array 20 along the return light path 70.

Since the electronic sensor 74 relies on the deviations -D- from zero positions, measured wavefront points must be matched with their zero positions. Marking the center lenslet of the array 20(or other key location) can be done to simplify registration of the microoptics array in that only a portion of the array is actually impinged upon by the generated wavefront 18, FIG. 1. The marking can be accomplished by several different approaches, such as by removal or blackening of the center or other lenslet, or by color encoding any number of the lenslets by conventional means, such as using a filter, etc. Registration of the microoptics array 20 could also be alternately performed by flickering at least one lenslet image, using an LCD (not shown) or other known method, such as replacement of the lenslet with an LED or a test target. This would allow the image of the array 20 to be easily correlated to a calibration image.

Modifications to the above system layouts can be easily imagined for folding either the return or the illumination light path or viewing path in order to optimally size the housing 40. In addition, the instrument can be powered by batteries 94 provided in the interior of the housing 40.

A second embodiment of the present invention employing the identical optical subassemblies 42, 44, 46 is herein described with reference to FIG. 9, in which similar parts are labeled with the same reference numerals for the sake of convenience. According to the present embodiment, there is disposed a housing (not shown) having a support plate 103 to which the components of the present assembly are attached by conventional means. The system includes an illumination housing 79 including a contained laser diode and suitable optics to project a beam through a beamsplitter 34 which directs the output of the laser diode toward the patient's eye 16, FIG. 1, of interest. In this instance, only a single folding mirror 106 is disposed between the first and second conjugate lenses 36, 38, thereby only folding the return path once. A viewfinder portion (not shown) is attached to a mount 108 which is elevated so as to allow the viewing axis to be obliquely angled relative to the illumination axis.

The second conjugate lens 38, according to this embodiment, is attached to an adjustable block 110 and includes a spacer 112 linking each with the microoptics array and the electronic sensor, the details of each also being the same as those described with respect to FIG. 8.

Figure 9:
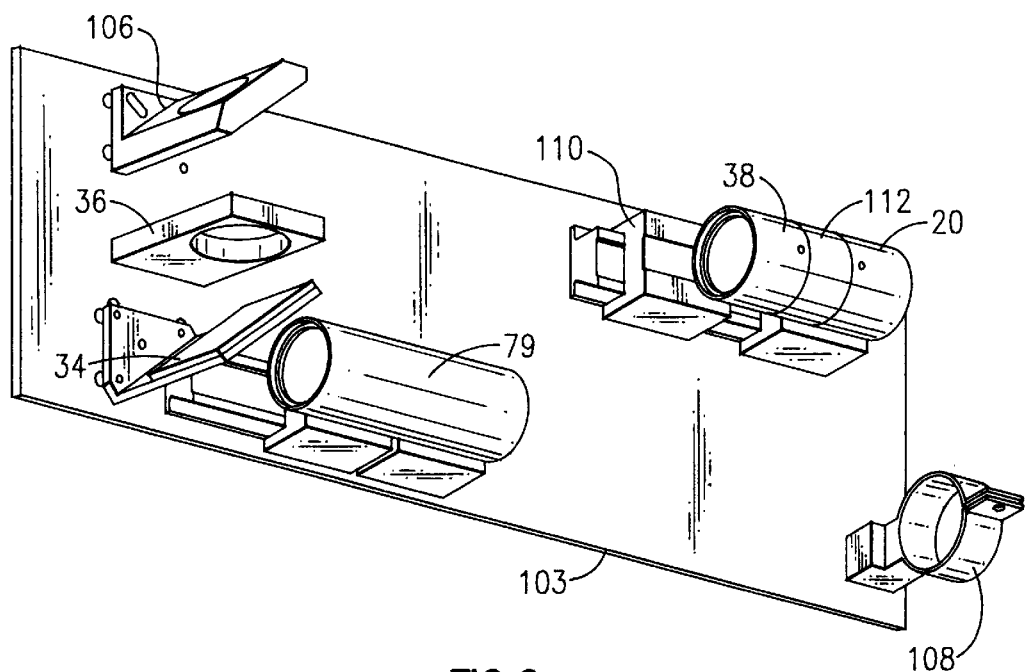
FIG. 9 is a partial interior view of an alternate preferred embodiment of a refractive error measuring apparatus according to the present invention.
Figures 10A, 10B:
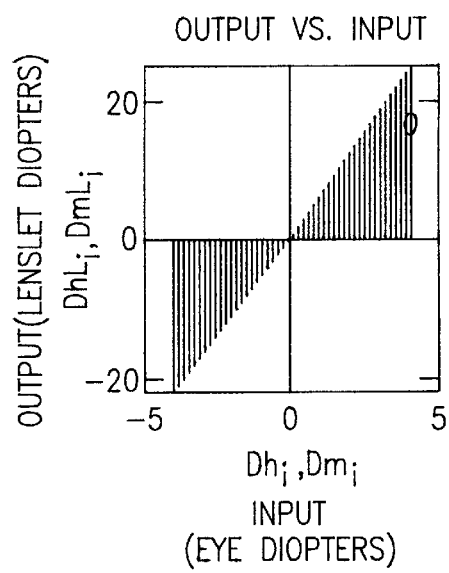
FIGS. 10(a) and 10(b) are tabular and graphical outputs of the refractive error measuring system of FIG. 8, illustrating the improved sensitivity of the device over a series of measurable diopters of an eye of interest.

Tabular and graphical outputs of each of the preceding described systems shown in FIGS. 8 and 9 are shown respectively in FIGS. 10(*a*) and 10(*b*). As is seen, the selection of the conjugate pair causes each of the measurable diopters to be manipulated at the microoptics array. The pitch of the microoptics array, the distance between the lenslets and the imaging substrate are selected to produce, according to this embodiment, a minified image which has increased optical power and to generate a readable displacement at the electronic sensor 74 for the following system parameters:

| | |
|---|---:|
| (WD) Working distance | 40 cm |
| Effective focal length (Microoptics array) | 7.9 mm |
| Pitch (microoptics array) | 0.2 mm |
| Focal length (first conjugate) | 150.765 mm |
| Focal length (second conjugate) | 63 mm |
| -A- | 17 mm | in which Dhi and Dmi refer to hyperopic and myopic diopter measured at the eye and DhLi and DmLi refer to hyperopic and myopic diopters measured at the microoptics array.

Figures 11A, 11B:
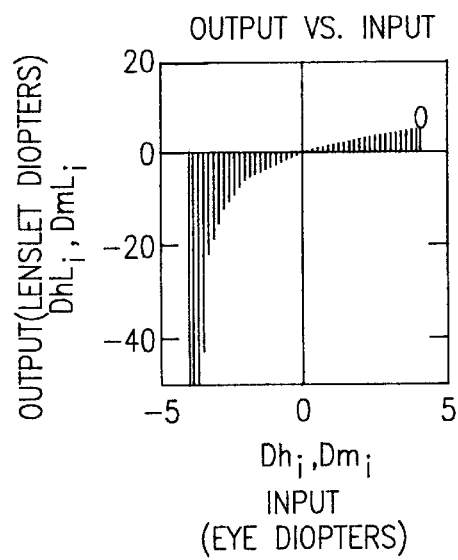
FIGS. 11(a) and 11(b) are corresponding tabular and graphical outputs of another refractive error measuring system according to the present invention, demonstrating the versatility of the arrangement to produce or accommodate a separate range of measurable eye diopters.

Other conjugate lens pairs, preferably having other than a 1:1 correspondence, can be utilized in conjunction with the pitch of the microoptics array 20 to provide a suitably sensitive refractive measuring system which can be skewed so as to provide superior results for a particular diopter range. For example, and using the same working distance and the same pitch and effective focal length of the microoptics array 20, a conjugate lens system having a first conjugate lens having an effective focal length of approximately 75 cm and a second conjugate lens having an effective focal length of approximately 50 cm produces the tabular and graphical outputs of FIG. 11(*a*) and 11(*b*).

Since corneal glare will be produced and potentially imaged onto the lenslet in addition to the wavefront of interest, consideration must be given to the glare's impact on the measurement. The distance (-A-) between the second conjugate lens and the lenslets is selected to produce glare in a selected focal plane. The selection of (-A-) will project corneal glare in a recognizable or predictable pattern at the lenslet and on the imaging plane (the imaging substrate) so that it can be removed optically or electronically. In the preferred embodiment, distance (-A-) is selected such that corneal glare is produced at a highly focused spot of light, which can be easily detected and removed from the remainder of the lenslet spots. Alternately, (-A-) can be selected such that glare is diffused substantially, creating only a faint background in the lenslet spot image. In the embodiments herein described (-A-) is approximately 17 mm and 15 mm, respectively.

PARTS LIST FOR FIGS. 1–11(*b*)

- 10 ideal eye
- 11 secondary source
- 12 generated wavefront
- 16 aberrated eye
- 18 generated wavefront
- 20 microoptics array
- 22 lenslet elements
- 24 imaging substrate
- 30 autorefractor system
- 32 light beam
- 34 beam splitter
- 36 conjugate lens
- 38 conjugate lens
- 40 instrument housing
- 42 illumination subassembly
- 44 measurement subassembly
- 46 viewing subassembly
- 48 viewing eye
- 50 laser diode
- 52 illumination axis
- 54 plano-convex singlet
- 55 aperture
- 56 plano-concave singlet
- 58 light beam
- 62 plano-concave singlet
- 64 plano-convex singlet
- 66 viewing axis
- 70 return light path
- 74 electronic sensor
- 76 LCD
- 78 support plate
- 79 illumination housing
- 80 folding mirror
- 81 port
- 82 folding mirror
- 83 housing
- 84 LED
- 85 vertical plate 86 support
87 aperture
88 folding mirror
89 viewing window
90 flashing fixation LEDs
94 battery
98 ultrasonic distance measuring sensor
103 support plate
106 folding milTor
108 mount
110 adjustable block
112 spacer Though the present invention has been described in terms of certain embodiments, it will be readily apparent that certain variations and modifications are possible within the metes and bounds of the concepts taught herein, and within the scope of the following appended claims.

We claim:

1. A compact apparatus for determining refractive aberrations of the eye, said apparatus comprising:
    a hand-held housing;
    illumination means including at least one source of illumination disposed in said housing for projecting a beam of light into the eye of a patient along an illumination axis, said beam forming a secondary source on the back of the eye for a return light path of an outgoing generated wavefront from said eye;
    measurement means disposed in said housing including light sensing means disposed along said light return path, said light sensing means including a light detection surface;
    at least one microoptics array disposed between said electronic sensor and said eye along said return light path, said microoptics array comprising a plurality of lenslets planarly disposed, said plurality of lenslets and said light detection surface being arranged parallel to each other and perpendicularly to said light return path, said microoptics array being positioned relative to said light sensing means so as to substantially focus portions of said formed wavefront onto said light detection surface, said measurement means further including means for detecting deviations in the positions of the substantially focused portions impinging on said light detecting surface so as to determine aberrations of said outgoing wavefront; and
    viewing means disposed in said housing for aligning the eye with the illumination axis.

2. Apparatus as recited in claim 1, including at least one pair of conjugate lenses disposed along said return light path and positioned between said eye and said at least one microoptics array to provide an effective working distance between said housing and an eye of a patient.

3. Apparatus as recited in claim 2, wherein said at least one pair of conjugate lenses include lenses having different effective focal lengths.

4. Apparatus as recited in claim 1, wherein said light source is disposed substantially orthogonal to said portion of said return light path.

5. Apparatus as recited in claim 2, wherein said working distance is in a range of approximately 1 to approximately 80 cm between said housing and an eye being examined.

6. Apparatus as recited in claim 5, wherein said working distance is approximately 40 cm.

7. Apparatus as recited in claim 2, wherein said at least one microoptics array, said at least one pair of conjugate lenses, and said light sensing means are fixedly attached in said housing.

8. Apparatus as recited in claim 7, wherein said illumination means are fixedly attached in said housing.

9. Apparatus as recited in claim 7, wherein said at least one pair of conjugate lenses are disposed in said housing and include a first and a second conjugate lens element, each said lens element being separated from one another by substantially the sum of their respective focal lengths.

10. Apparatus as recited in claim 9, wherein a range of measurable diopters of said eye are manipulated relative to corresponding diopters present at said at least one microoptics array due the generated wavefront passing through said at least one pair of conjugate lenses.

11. Apparatus as recited in claim 10, including a single pair of conjugate lenses in which the first conjugate lens element disposed closer to the eye being examined has an effective focal length which is greater than the effective focal length of the second conjugate lens element.

12. Apparatus as recited in claim 11, wherein the diopters of the formed wavefront presented at said at least one microoptics array are manipulated to be greater than the corresponding measurable diopters of the eye being examined in order to optimize the capability of determining refractive error over a particular diopter range.

13. Apparatus as recited in claim 12, wherein the range of measurable diopters is approximately −20 to +20 diopters.

14. Apparatus as recited in claim 13, wherein the range of measurable diopters is approximately −6 to +6 diopters.

15. Apparatus as recited in claim 2, including position finding means for signaling when an appropriate working distance has been attained between the housing and an eye being examined.

16. Apparatus as recited in claim 15, wherein said position finding means includes an ultrasonic sensor disposed on said housing, said sensor having means for producing at least one audible signal dependent on the distance between said housing and a subject eye.

17. Apparatus as recited in claim 1, wherein said viewing means is disposed along a viewing axis, said viewing axis being arranged at an oblique angle relative to said illumination axis.

18. Apparatus as recited in claim 1, wherein said viewing means includes aiming means, said aiming means including an alignment pattern and means for projecting said alignment pattern along said viewing axis onto the back of the eye.

19. Apparatus as recited in claim 1, wherein said illuminating means includes a monochromatic light source.

20. Apparatus as recited in claim 19, wherein said monochromatic light source is a laser diode.

21. Apparatus as recited in claim 19, wherein said monochromatic light source projects a light beam having a wavelength in the range of approximately 750–850 nm.

22. Apparatus as recited in claim 1, including a beamsplitter disposed along said return light path and said illuminating axis, said beamsplitter allowing a portion of said return light path to be angularly disposed relative to said illuminating axis.

23. Apparatus as recited in claim 1, wherein said lenslets of said array has a pitch between adjacent lenslets which is less than approximately 2 mm.

24. Apparatus as recited in claim 1, including means for defining the portion of said at least one microoptics array onto which said generated wavefront impinges when extended onto said light detecting surface.

25. Apparatus as recited in claim 24, wherein at least one of said lenslets is color encoded.

26. Apparatus as recited in claim 24, including means for masking at least one of said lenslets.

27. Apparatus as recited in claim 24, wherein said at least one of said lenslets is removed in order to provide an alignment orientation of said array for mapping said wavefront.

28. Apparatus as recited in claim 24, wherein the center lenslet is removed from said array.

29. Apparatus as recited in claim 1, including means for manipulating corneal glare from light impinging on said at least one microoptics array along said light return path so as to image glare to a predictable form.

30. Apparatus as recited in claim 29, wherein said corneal glare manipulating means includes means for setting the distance between said at least one microoptics array and the conjugate lens closest to said at least one microoptics array in order to vary the focus thereof.

31. Apparatus as recited in claim 1, wherein said illuminating means includes light adjustment means for varying the position of the formed point source so as to focus onto the back of an aberrated eye.

32. Apparatus as recited in claim 31, wherein said adjustment means includes means for one of either converging and diverging the projected beam of light.

33. Apparatus as recited in claim 1, wherein said viewing means includes means for producing a magnified image.

34. Apparatus as recited in claim 1, including means for fixating the eye being examined.

35. Apparatus as recited in claim 34, wherein said fixating means includes at least one flashing LED disposed along said illuminating axis.

36. Apparatus as recited in claim 35, wherein said fixating means includes an audible signal device disposed in said housing for cuing a subject being examined.

37. Apparatus as recited in claim 35, wherein said fixation means includes at least one still image mounted so as to be viewable by the subject when looking toward said apparatus.

38. Apparatus as recited in claim 37, wherein said position finding means include projection means for projecting at least two images which merge onto a subjects field of view in a recognizable shape at a predetermined working distance.

39. Apparatus as recited in claim 37, wherein said position finding means includes a light emitter and detector oriented angularly relative to each other such that one of the reflected position and intensity of light detected by the detector from said emitter is a known function.

40. Apparatus as recited in claim 37, wherein said position finding means includes at least one wave generator capable of generating a modulated wave reflected toward a subject and detection means for detecting a return wave, said detection means including means for detecting one of the intensity and phase of the return wave as a know function of the distance between said wave generator and the subject.

41. Apparatus as recited in claim 1, including means for displaying data measured by said light detecting surface.

42. A method of measuring refractive eye error, said method comprising:
projecting a beam of light into an eye of interest, said light producing a secondary source and generating a representative wavefront from the eye along a return light path;
aligning said eye with said beam of projected light;
directing said generated wavefront through a pair of conjugate lenses onto at least one microoptics array having a series of planarly disposed lenslet elements, said conjugate lenses and said lenslet array being disposed along said return light path;
substantially focusing incremental portions of said generated wavefront passing through said lenslet elements onto an imaging substrate; and
measuring the deviations in the incremental portions of said generated wavefront on said imaging substrate so as to measure refractive error in the eye of interest.

43. A method as recited in claim 42, wherein said at least one pair of conjugate lenses include lenses of different effective focal lengths, said method including the step of separating said pair of conjugate lenses along said return light path by substantially the sum of the respective focal lengths of said lenses.

44. A method as recited in claim 43, including the steps of minifying the generated wavefront beam diameter impinging on said at least one microoptics array by using a pair of conjugate lenses in which the conjugate lens closest to the eye of interest has an effective focal length which is greater than the focal length of the remaining conjugate lens so as to increase the optical power of light received by said lenslets.

45. A compact apparatus for determining refractive aberrations of the eye, said apparatus comprising:
a hand-held housing; illumination means disposed in said housing for projecting a beam of light into the eye of a patient along an illumination axis, said beam forming a secondary source on the back of the eye for a return light path of a generated wavefront from said eye;
measurement means disposed in said housing including an electronic sensor disposed along said light return path, said electric sensor having an imaging substrate;
alignment means for aligning the eye with the illumination axis, said alignment means including a viewing port arranged obliquely with respect to said illumination means along a viewing axis and means for directing an alignment guide along said viewing axis to said eye;
at least one microoptics array disposed between said electric sensor and said eye along said return light path, said at least one microoptics array comprising a plurarality of lenslets planarly disposed, said plurality of lenslets and said imaging substrate being arranged parallel to each other and perpendicuarly to said light return path, said at least one microoptics array being positioned relative to said electronic sensor so as to substantially focus portions of said formed wavefront onto said imaging substrate, said measurement means further including means for detecting deviations in the positions of the substantially focused portions impinging on said imaging substrate so as to determine aberrations of said outgoing wavefront, and
at least one pair of conjugate lenses disposed along said light return path between the eye of interest and said at least one microoptics array, each of said conjugate lenses having different focal lengths for allowing said housing to be used at a suitable working distance from a patient, said working distance being greater than 1 cm.

46. A method as recited in claim 42, wherein said aligning step includes the steps of viewing said eye along a viewing axis which is inclined obliquely relative to said illumination axis and targeting an alignment pattern along said viewing axis in relation to said eye and said projected beam.

47. Apparatus as recited in claim 45, wherein said suitable working distance is in the range of approximately 5 cm to approximately 80 cm.

\* \* \* \* \*

UNITED STATES PATENT AND TRADEMARK OFFICE
CERTIFICATE OF CORRECTION

PATENT NO.    : 6,007,204
DATED         : December 28, 1999
INVENTOR(S)   : Fahrenkrug et al.

It is certified that error appears in the above-identified patent and that said Letters Patent is hereby corrected as shown below:

Column 15,
Lines 29 and 32, please delete "35" and insert -- 34 --.
Lines 36, 39 and 44, please delete "37" and insert -- 15 --.

Signed and Sealed this

Eighteenth Day of November, 2003

JAMES E. ROGAN
*Director of the United States Patent and Trademark Office*